United States Patent
Kamohara et al.

(10) Patent No.: US 6,568,937 B2
(45) Date of Patent: May 27, 2003

(54) ROOT CANAL FILLING MATERIAL

(75) Inventors: Hiroshi Kamohara, Itabashi-ku (JP); Takaharu Takeshita, Itabashi-ku (JP)

(73) Assignee: GC Corporation, Tokyo (JP)

( * ) Notice: Subject to any disclaimer, the term of this patent is extended or adjusted under 35 U.S.C. 154(b) by 0 days.

(21) Appl. No.: 09/928,311

(22) Filed: Aug. 14, 2001

(65) Prior Publication Data

US 2002/0051952 A1 May 2, 2002

(30) Foreign Application Priority Data

Sep. 1, 2000 (JP) ........................................ 2000-265441

(51) Int. Cl.[7] .................................................. A61C 5/00
(52) U.S. Cl. ....................................... 433/228.1; 106/35
(58) Field of Search .............................. 433/228.1, 226, 433/224; 106/35; 523/116, 115

(56) References Cited

U.S. PATENT DOCUMENTS 4,740,245 A * 4/1988 Futami et al. ................. 106/35
6,028,125 A * 2/2000 Combe et al. ............... 523/115

OTHER PUBLICATIONS

Derwent Publications, AN 1990–256395, JP 2–178206, Jul. 11, 1990.

* cited by examiner

*Primary Examiner*—Kevin Shaver
*Assistant Examiner*—Melba Bumgarner
(74) *Attorney, Agent, or Firm*—Oblon, Spivak, McClelland, Maier & Neustadt, P.C.

(57) ABSTRACT

To provide a root canal filling material, which is high in strength, is hardly bent, is easy for root canal filling operation, is properly deformed during press contact, is high in adhesion and superior in sealing properties between root canal filling material each other or between a root canal filling material and a root canal wall, and is provided with proper radiopacity, the root canal filling material is constructed of (A) 1 to 50% by weight of one or two or more thermoplastic resins selected from trans-polyisoprene, polyethylene, polypropylene, and a copolymer of polyethylene and polypropylene; (B) 0.1 to 20% by weight of a styrene block copolymer; (C) 0.1 to 10% by weight of a paraffin wax; and (D) 30 to 95% by weight of one or two or more inorganic fillers selected from zinc oxide, barium sulfate, zirconium oxide, and titanium oxide.

3 Claims, No Drawings

ROOT CANAL FILLING MATERIAL

BACKGROUND OF THE INVENTION

1. Field of the Invention

The present invention relates to a root canal filling material that is used for the root canal treatment in the dental therapy. More particularly, the invention relates to a root canal filling material that is usually formed in a point-like state and provided, is not bent when inserted into the root canal, and is extremely good in filling properties within the root canal.

2. Description of the Conventional Art

In order to carry out the therapy of dental pulp disease and apical periodontitis, is taken a treatment in which a substance that is materially stable is filled in the root canal after extirpation of dental pulp, thereby keeping a tooth root harmless to a periodontal tissue. At this time, the filling material to be filled within the root canal, that is stable to living bodies, is a root canal filling material. At present, of those root canal filling material, is most widely used a point-like filling material called a gutta-percha point. This filling material is composed mainly of gutta-percha as a natural resin and zinc white. Since this filling material is stable to living bodies, it is widely used as a root canal filling material.

While the method for carrying out the root canal filling using this gutta-percha point includes various methods, a filling method called a lateral condensation method is most commonly spread. This lateral condensation method is achieved by using two types of gutta-percha points having a different thickness from each other (a master point and an accessory point). In this filling method, the master point is first filled, and the accessory point is then filled, thereby filling a gap, i.e., the gutta-percha points are filled while applying a pressure.

However, the root canal is not always simple in shape and is often curved. For this reason, the gutta-percha point is required to have a hardness to some extent and to be resistant to the pressure applied when inserted into the root canal. But, when the hardness of the gutta-percha point is increased excessively, the point per se is likely broken, and it is difficult that the point reaches near the root apex. As a result, the root canal filling has been liable to be incomplete.

Further, when the gutta-percha point is inserted within the root canal, there is employed an operation for minutely filling the gutta-percha point by repeating the procedures in which the gutta-percha point is brought into press contact with a metallic long and slender instrument called a spreader and deformed slightly. However, in this filling operation, when the gutta-percha point is not deformed properly, it is very difficult to achieve the filling by the spreader. As a result, not only the filling rate of the gutta-percha point within the root canal has been lowered, but also there has been a possibility to induce a change of a morbid state caused by the generation of a gap. In addition, the adhesion between the gutta-percha points each other, or between the gutta-percha point and the root canal wall during the press contact is insufficient. As a result, the sealing properties have been poor so that a change of a morbid state has been possibly induced, too. Moreover, in order to facilitate the confirmation by X-rays, it is one of important characteristics required for the root canal filling material to impart sufficient radiopacity to the root canal filling material.

SUMMARY OF THE INVENTION

Thus, the present invention is aimed at developing a root canal filling material to be usually formed in a point-like state and provided, which is higher in strength than gutta-percha point currently used for root canal filling, is hardly broken, is easy for root canal filling operation, is properly deformed during press contact, is high in adhesion and superior in sealing properties between root canal filling material each other, or between a root canal filling material and a root canal wall, and is provided with proper radiopacity.

The root canal filling material that is used in the present invention is a root canal filling material comprising one or two or more thermoplastic resins selected from trans-polyisoprene, polyethylene, polypropylene, and a copolymer of polyethylene and polypropylene, to which are added a styrene block copolymer as a component for not only improving the breakage resistance but also improving the adhesion during press contact; a paraffin wax as a component for imparting proper plasticity; and one or two or more inorganic fillers selected from zinc oxide, barium sulfate, zirconium oxide, and titanium oxide, as a component for imparting proper hardness and radiopacity within the root canal.

Specifically, the present invention is concerned with a root canal filling material comprising (A) 1 to 50% by weight of one or two or more thermoplastic resins selected from trans-polyisoprene, polyethylene, polypropylene, and a copolymer of polyethylene and polypropylene; (B) 0.1 to 20% by weight of a styrene block copolymer; (C) 0.1 to 10% by weight of a paraffin wax; and (D) 30 to 95% by weight of one or two or more inorganic fillers selected from zinc oxide, barium sulfate, zirconium oxide, and titanium oxide.

DESCRIPTION OF THE PREFERRED EMBODIMENTS

In the root canal filling material according to the present invention, the component (A) is a component for imparting basic strength and formability as the root canal filling material. Of the thermoplastic resins as the component (A), trans-polyisoprene is a thermoplastic resin, which is present as a major component of gutta-percha as a natural resin, has slight rubber elasticity, and is softened at about 70° C. On the other hand, polyethylene, polypropylene, and the copolymer of polyethylene and polypropylene are a resin generally used in films and various moldings. Since these thermoplastic resins are generally made into a hard molding but do not have rubber elasticity very much, they are a material that has hitherto been not able to be used for the root canal filling material required to have proper flexibility. However, it has become possible to impart proper flexibility, plasticity, and filling properties when combined with the component (B) and the component (C) as described later.

The component (A) is one or two or more thermoplastic resins selected from trans-polyisoprene, polyethylene, polypropylene, and a copolymer of polyethylene and polypropylene. It is necessary that the content of the component (A) is 1 to 50% by weight. When the content of the component (A) is less than 1% by weight, not only it is impossible to impart sufficient strength to the root canal filling material, but also the root canal filling material is very brittle, and it is difficult to achieve the filling operation within the root canal. On the other hand, when the content of the component (A) exceeds 50% by weight, since the amount of the inorganic filler as the component (D) to be compounded as described later, is small, the radiopacity is lowered so that it becomes difficult to undergo the confirmation by X-rays.

The component (B) is a component for imparting the characteristic features of the present invention, i.e., the root canal filling material is hardly broken during the root canal filling operation, and the adhesion between the root canal filling material each other, or between the root canal filling material and the root canal wall during the press contact is enhanced. For the styrene block copolymer as the component (B), can be used a block copolymer of polystyrene and polybutadiene, a block copolymer of polystyrene and polyisoprene, and a block copolymer of polystyrene and a polyolefin. Since the component (B) per se has elasticity as in vulcanized rubbers, when used together with the component (A), it becomes possible to impart proper flexibility, thereby imparting a characteristic that the root canal filling material is hardly broken during the root canal filling.

In addition, when the component (B) is used together with the component (C) as described later, not only the adhesion between the root canal filling material each other, or between the root canal filling material and the root canal wall is improved, and the sealing properties are improved, but also the compatibility with the above-described component (A) is very good. Therefore, there gives rise to an effect that the actual production is easy. It is necessary that the content of the component (B) is 0.1 to 20% by weight. When the content of the component (B) is less than 0.1% by weight, the root canal filling material is liable to be broken during the filling operation. On the other hand, when the content of the component (B) exceeds 20% by weight, in the case where the root canal filling material is formed in a point-like state, the flexibility is excessively large, so that the point hardly reaches the root apex.

The paraffin wax as the component (C) is effective for imparting proper flexibility to the root canal filling material and making the filling operation easy. The component (C) is compounded in an amount of 0.1 to 10% by weight. When the content of the component (C) is less than 0.1% by weight, the plasticity is too low, so that the filling operability within the root canal is lowered. On the other hand, when the content of the component (C) exceeds 10% by weight, the root canal filling material is brittle so that it is liable to be broken.

The component (D) is one or two or more inorganic fillers selected from zinc oxide, barium sulfate, zirconium oxide, and titanium oxide, and imparts strength as well as radiopacity to the root canal filling material. The content of the component (D) is 30 to 95% by weight. When the content of the component (D) is less than 30% by weight, the hardness is lowered, and the radiopacity is insufficient. On the other hand, when the content of the component (D) exceeds 95% by weight, not only the root canal filling material is excessively brittle, but also the viscosity during the production is too high, whereby the productivity of the root canal filling material is lowered.

In the root canal filling material according to the present invention, so far as its characteristics are not lost, various inorganic or organic coloring agents or bactericides maybe used.

Next, the root canal filling material according to the present invention will be described in more detail with reference to the following Examples, but it should not be construed that the invention is limited thereto.

EXAMPLE 1

| | |
|---|---|
| Trans-polyisoprene: | 15% by weight |
| Block copolymer of polystyrene and polyisoprene: | 1% by weight |
| Paraffin wax: | 1% by weight |
| Zinc oxide: | 83% by weight |

The above components were weighed and mixed upon heating under conditions at 150 to 180° C. by means of a pressure kneader, to prepare a root canal filling material. This root canal filling material was formed in a point-like state, and the point-like molding was tested for bending strength, sealing properties and easiness for filling operation. The results obtained are summarized and shown in Table 1. Each of the test methods is as follows.

(a) Bending Strength:

The root (a portion having the maximum diameter) of the point-like molding was mounted in a rheometer (manufactured by Sun Kagaku Co., Ltd.), and a load was applied from the tip at a crosshead speed of 20 mm/min. And, the maximum load until the molding had been broken was measured.

(b) Sealing Properties:

A standard human maxillary lateral incisor, which, after tooth extraction, had been stored in a 10% formalin solution, was used as a sample. The incisal edge of the sample was cut, and the pulp chamber was opened, followed by subjecting to usual root canal enlargement operation to for root canal formation. The above-described point-like molding was filled within the thus formed root canal using a spreader in a lateral condensation method, and then immersed in a 0.6% Rhodamine aqueous solution in a thermostat at 37° C. for 7 days. Thereafter, the point was removed from the root canal, and the length of the coloring matter invaded within the root canal was measured. The shorter the invading length, the better the sealing properties are.

(c) Easiness for Filling Operation:

In the filling operation by means of a spreader during the test of sealing properties as described above, the easiness for the filling was evaluated. The evaluation was made according to the following criteria. That is, when the point-like molding was charged by means of a spreader, the case where the filling could be easily achieved is designated as "A", and the case where the point-like molding itself was not substantially deformed even using the spreader, and the filling was very difficult, is designated as "B", respectively.

EXAMPLE 2

| | |
|---|---|
| Copolymer of polyethylene and propylene: | 40% by weight |
| Block copolymer of polystyrene and polyolefin (ethylene/propylene copolymer): | 20% by weight |
| Paraffin wax: | 10% by weight |
| Barium sulfate: | 30% by weight |

The above components were weighed and mixed upon heating under conditions at 150 to 180° C. by means of a pressure kneader, to prepare a root canal filling material. Using this root canal filling material, various testes were carried out in the same manner as in Example 1. The results obtained are summarized and shown in Table 1.

EXAMPLE 3

| | |
|---|---|
| Polypropylene: | 3% by weight |
| Block copolymer of polystyrene and polyisoprene: | 7% by weight |
| Paraffin wax: | 0.4% by weight |
| Zinc oxide: | 29.6% by weight |
| Zirconium oxide: | 60% by weight |

The above components were weighed and mixed upon heating under conditions at 150 to 180° C. by means of a pressure kneader, to prepare a root canal filling material. Using this root canal filling material, various testes were carried out in the same manner as in Example 1. The results obtained are summarized and shown in Table 1.

EXAMPLE 4

| Trans-polyisoprene: | 10% by weight |
|---|---|
| Copolymer of polyethylene and polypropylene: | 5% by weight |
| Block copolymer of polystyrene and polyisoprene: | 3% by weight |
| Paraffin wax: | 1% by weight |
| Zinc oxide: | 80.5% by weight |
| Red oxide: | 0.5% by weight |

The above components were weighed and mixed upon heating under conditions at 150 to 180° C. by means of a pressure kneader, to prepare a root canal filling material. Using this root canal filling material, various testes were carried out in the same manner as in Example 1. The results obtained are summarized and shown in Table 1.

Comparative Example 1

| Trans-polyisoprene: | 15% by weight |
|---|---|
| Zinc oxide: | 85% by weight |

The above components were weighed and mixed upon heating under conditions at 150 to 180° C. by means of a pressure kneader, to prepare a root canal filling material. Using this root canal filling material, various testes were carried out in the same manner as in Example 1. The results obtained are summarized and shown in Table 1.

Comparative Example 2

| Trans-polyisoprene: | 14% by weight |
|---|---|
| Paraffin wax: | 1% by weight |
| Zinc oxide: | 85% by weight |

The above components were weighed and mixed upon heating under conditions at 150 to 180° C. by means of a pressure kneader, to prepare a root canal filling material. Using this root canal filling material, various testes were carried out in the same manner as in Example 1. The results obtained are summarized and shown in Table 1.

Comparative Example 3

Using a commercially available product, "GC Guttapercha Point" (made by GC Corporation), various testes were carried out in the same manner as in Example 1. The results obtained are summarized and shown in Table 1.

TABLE 1

| | Example No. | | | | Comparative Example No. | | |
|---|---|---|---|---|---|---|---|
| | 1 | 2 | 3 | 4 | 1 | 2 | 3 |
| Bending strength (g) | 42 | 39 | 41 | 42 | 22 | 21 | 19 |
| Sealing properties (length of coloring matter invaded: mm) | 1.3 | 1.5 | 1.3 | 1.4 | 2.9 | 2.8 | 3.3 |
| Easiness for filling operation | A | A | A | A | B | B | B |

As is clear from Table 1, the root canal filling material according to the present invention have characteristics such that they are high in strength and are hardly bent, as compared with the currently commercially available guttapercha point of Comparative Example 3. Further, it has also been confirmed that, in the root canal filling material according to the present invention, since the adhesion between the root canal filling material each other, or between the root canal filling material and the root canal wall is better, the sealing properties are good, and the filling operation is superior, as compared with the currently commercially available gutta-percha point. On the other hand, in any of Comparative Example 1 containing neither styrene block copolymer nor paraffin wax and Comparative Example 2 containing no styrene block copolymer, the prepared root canal filling material were liable to be bent, were poor in sealing properties, and were very difficult for filling operation.

In the light of the above, the root canal filling material according to the present invention is high in strength, is hardly bent, is high adhesion between the root canal filling material each other, or between the root canal filling material and the root canal wall during press contact and hence, is superior in sealing properties, and is easy for the root canal filling operation, as compared with the gutta-percha point currently used for the root canal filling. Accordingly, the root canal filling material according to the present invention can markedly improve the respective characteristics as required for the root canal filling material and is greatly valuable in contributing to the dental field.

While the invention has been described in detail and with reference to specific embodiments thereof, it will be apparent to one skilled in the art that various changes and modifications can be made therein without departing from the spirit and scope thereof.

What is claimed is:

1. A root canal filling material consisting essentially of:
   (A) 1 to 50% by weight of one or more thermoplastic resins selected from the group consisting of trans-polyisoprene, polyethylene, polypropylene, and a copolymer of polyethylene and polypropylene;
   (B) 0.1 to 20% by weight of a styrene block copolymer;
   (C) 0.1 to 10% by weight of a paraffin wax; and
   (D) 30 to 95% by weight of one or more inorganic fillers selected from the group consisting of zinc oxide, barium sulfate, zirconium oxide, and titanium oxide.

2. The root canal filling material of claim 1, wherein (B) comprises a block copolymer of polystyrene and a polyolefin.

3. The root canal filling material of claim 1, wherein (B) comprises a block copolymer selected from the group consisting of, block copolymer of polystyrene and polybutadrene, and block copolymer of polystyrene and polyisoprene.

* * * * *